United States Patent [19]

Cvetovich

[11] Patent Number: 5,362,863
[45] Date of Patent: Nov. 8, 1994

[54] PROCESS FOR THE PREPARATION OF 4'-AMINO AVERMECTIN COMPOUNDS

[75] Inventor: Raymond Cvetovich, Scotch Plains, N.J.

[73] Assignee: Merck & Co., Inc., Rahway, N.J.

[21] Appl. No.: 128,936

[22] Filed: Sep. 29, 1993

[51] Int. Cl.$^5$ .................. C07H 17/04; A61K 31/70
[52] U.S. Cl. .................................................. 536/7.1
[58] Field of Search ............... 536/7.1; 514/30, 450; 549/264

[56] References Cited

U.S. PATENT DOCUMENTS

| | | | |
|---|---|---|---|
| 4,427,663 | 1/1984 | Mrozik | 424/180 |
| 4,874,749 | 10/1989 | Mrozik | 514/30 |
| 5,008,191 | 4/1991 | Okazaki et al. | 435/124 |
| 5,212,322 | 5/1993 | Okazaki et al. | 549/265 |

FOREIGN PATENT DOCUMENTS

| | | |
|---|---|---|
| 0301806 | 7/1988 | European Pat. Off. . |
| 0465121 | 6/1991 | European Pat. Off. . |
| 0465121A1 | 1/1992 | European Pat. Off. ............. 536/7.1 |

OTHER PUBLICATIONS

Pure & Appl. Chem., vol. 62, No. 7, pp. 1231–1240, 1990, by M. H. Fisher.

*Primary Examiner*—Johnnie R. Brown
*Assistant Examiner*—Howard C. Lee
*Attorney, Agent, or Firm*—David L. Rose; Joseph F. DiPrima

[57] ABSTRACT

A 4"-oxoavermectin intermediate is reductively aminated using hexa- or heptamethyldisilazane and sodium borohydride to produce a 4"-amino (or methylamino)avermectin. The 4"- aminoavermectin is a useful intermediate in the preparation of N-acyl derivatives. The compounds are useful as agricultural and animal health insecticides and parasiticides.

1 Claim, No Drawings

PROCESS FOR THE PREPARATION OF 4'-AMINO AVERMECTIN COMPOUNDS

BACKGROUND OF THE INVENTION

In the synthesis of 4"-amino avermectin derivatives, the introduction of the amino group through a reductive amination of the 4"-oxo intermediate, using traditional imine formation and reduction techniques such as ammonia or methylamine and $NaBH_3CN$ was achieved in poor yields of between 20 and 65%. These poor yields were due to incomplete imine formation, base-induced epimerization at the 2-position and cyanoamino formation. The instant process is a significant improvement over other prior processes achieving yields of about 85–90% for the reductive amination. The compounds produced by the novel process of this invention and the prior processes for their preparation are known in U.S. Pat. Nos. 4,427,663 and 4,874,749.

SUMMARY OF THE INVENTION

This invention is concerned with an improved process for the preparation of 4"-amino avermectin compounds. Specifically the improved process converts the 4"-oxo avermectin compound into the 4"-amino or substituted amino compound via a reductive amination process using hexa-or heptamethyldisilazane followed by sodium borohydride and ethanol. Thus, it is an object of this invention to describe the improved process for the preparation of 4"-amino and substituted amino avermectin. An additional object is to describe the specific reaction conditions for the preparation of such compounds. A further object is to describe the improved methods used to prepare the protected intermediates used as intermediates in the instant process. Still further objects will become apparent from a reading of the following description.

DETAILED DESCRIPTION OF THE INVENTION

The novel process of this invention is reductive amination of an appropriately protected 4"-oxoavermectin $B_1$.

The process comprises: (a) treating the appropriately protected 4"-oxoavermectin $B_1$ of structural formula I:

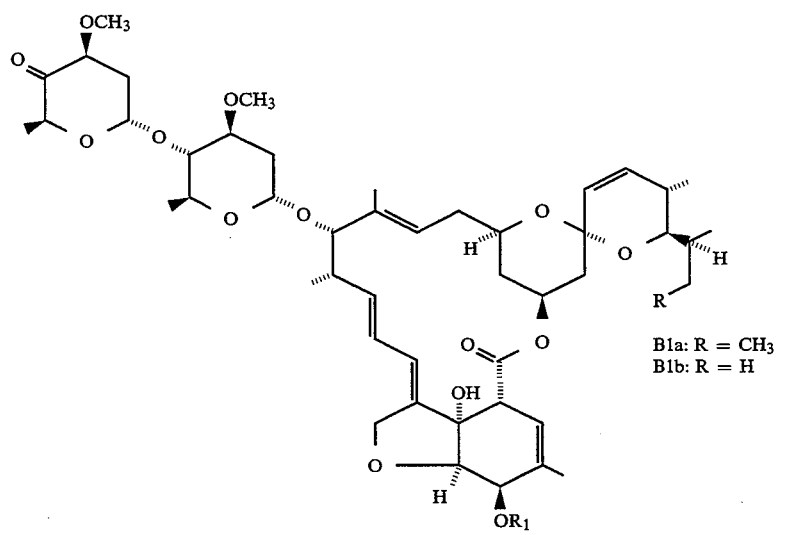

$R_1 = CO_2CH_2CH=CH_2$ or $Si(CH_3)_2C(CH_3)_3$ with a compound of structural formula:

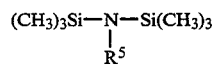

wherein $R^5$ is H (hexamethyldisilazane) or —$CH_3$ (heptamethyldisilazane) and a Lewis acid in an organic solvent such as isopropyl acetate; (b) adding $NaBH_4$ and a $C_{1-3}$ alkanol to produce the 4"-aminoor 4"-methylamino avermectin respectively of structural formulae II:

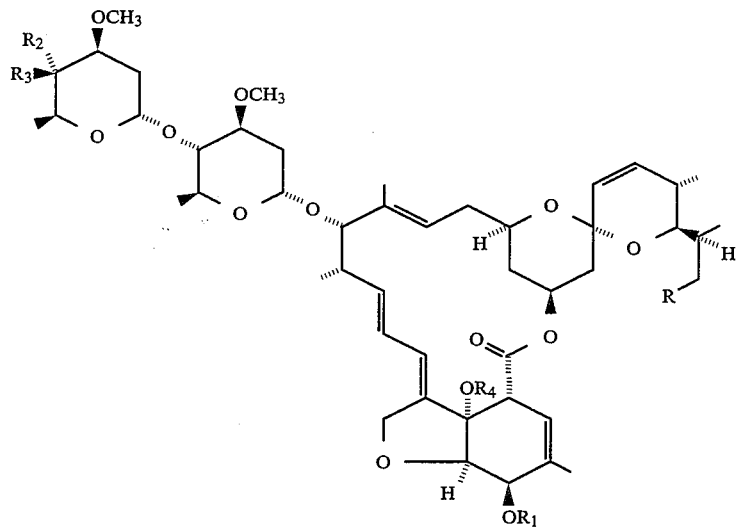

with HxMDS  
$R^5 = H$
- a: $R_2 = H$, $R_3 = NH_2$, $R_4 = H$
- b: $R_2 = H$, $R_3 = NH_2$, $R_4 = TMS$
- c: $R_2 = NH_2$, $R_3 = H$, $R_4 = H$ with HpMDS  
$R^5 = CH_3$
- d: $R_2 = H$, $R_3 = CH_3NH$, $R_4 = TMS$
- e: $R_2 = CH_3NH$, $R_3 = H$, $R_4 = TMS$;

and (c) hydrogenolysing IIa and/or IIb to produce IIf or hydrogenolysing IId to produce IIg by treatment with $NaBH_4$ in a $C_{1-3}$ alkanol preferably methanol or ethanol in the presence of $(Ph_3P)_4Pd(O)$ IIf: $R_2=H$, $R_3=NH_2$, $R_1$ and $R_4=H$ IIg: $R_2=H$, $R_3=NHCH_3$, $R_1$ and $R_4=H$.

The appropriately protected 4″-oxoavermectin is one in which the $C_5$-hydroxy group is protected while the $C_7$- and $C_4″$-hydroxyl groups remain unprotected.

Protection of the 5-hydroxy group in the presence of the $C_7$ and $C_4$-hydroxyl groups of avermectin $B_1$ using t-butyldimethylsilyl chloride (TBDMSCI) typically gives an 87:13 ratio of mono:bis(5:4″) protected avermectin $B_1$, with no reaction at the highly hindered 7-hydroxyl group. As an alternative to silicon based protecting groups, a selective acylation with allyl chloroformate was explored. The reaction of allyl chloroformate with avermectin $B_1$ to prepare the monoprotected avermectin in the presence of triethylamine (TEA) shows chemosensitivity to the solvent chosen as the reaction vehicle. In THF and ethyl acetate, poor selectivity results (~N50:50), but chlorinated solvents such as methylene chloride and (1,1,1)-trichloroethane produce product ratios of 93:7 (mono:bis). A remarkable increase in selectivity in non-chlorinated solvent is observed when N,N,N′,N′-tetramethyl-1,2-ethylenediamine (TMEDA) is substituted for TEA. In THF or t-butyl methyl ether (MTBE) the mono:bis ratio of protected avermectins increases from 50:50 to 97:3.

The subsequent oxidation of 5-O-protected avermectin $B_1$ is smoothly accomplished using the phenyl dichlorophosphate (PDCP)-mediated Pfitzner-Moffat oxidation. This oxidation works equally well in methylene chloride or in non-chlorinated solvents like isopropyl acetate (i-PrOAc), affording 4″-oxoavermectin-$B_1$ in 90% yield, requiring no need of purification prior to reductive aminations.

Reductive amination of 4″-oxo-5-O-t-butyl-dimethylsilylavermectin (TBDMS AVM $B_1$) using $CH_3NH_2$/acetic acid in THF to generate the corresponding imine, followed by reduction with $NaCNBH_3$ in ethanol, gives rise to a complex mixture containing the desired 4″-epi-$CH_3NH$-5-O-TBDMS AVM $B_1$ (50%), the isomeric 4″-$CH_3NH$-5-O-TBDMS AVM $B_1$ (10%), 4″-CN-4″-$CH_3NH$-5-O-TBDMS AVM $B_1$ (10%), and an epimeric mixture of 4″-hydroxy AVM $B_1$'s(10–30%, resulting from the reduction of the ketone remaining due to incomplete imine formation). In addition, epimerization at the $C_2$ position (5–20%) also occurs during the course of the reaction, with greater amounts present in samples that are aged longer or at higher temperatures during imine formation. Imine reduction with $NaBH_4$ increases the stereoselectivity of hydride addition and eliminates the cyano-amine, but $C_2$ epimerization and incomplete imine formation remain as the major sources of yield loss.

Similar reductive amination using ammonium acetate/$NaBH_4$ to make 4″-epi-$NH_2$-5-O-TBDMS AVM $B_1$ gives maximum yields of 25%, with the greatest loss occurring from incomplete imine formation. The use of stronger acid (ammonium chloride), molecular sieves, or a variety of Lewis acids fails to significantly influence the outcome.

In the novel process of the present invention the crude 4″-oxo-5-$OR^1$ $B_1$ and hexamethyldisilazane or heptamethyldisilazane (about 3–4 moles/mole of substrate) and a Lewis acid such as $ZnCl_2$, $ZnBr_2$ or $Zn(O-COCF_3)_2$ in an organic solvent such as isopropyl acetate THF, or toluene is warmed to about 40°–60° C. for about 3 to 5 hours. After cooling to about 0°–10° C., $NaBH_4$ (about 3–4 moles/mole of substrate) in ethanol is added while maintaining the temperature at less than about 10° C. at which temperature it is aged for about 0.5 to about 2 hours. The intermediates, 4″-epi-amino-5-O—$R^1$-4″-deoxyavermectin $B_1$ and 4″-epi-methylamino-5-O—$R^1$-7-O-trimethylsilyl-4″-deoxyavermectin $B_1$ are isolated by dropwise addition of dilute acetic acid followed by adjustment to about pH 8 with a base such as sodium or potassium hydroxide, removal of precipitated zinc salts and extraction with an organic solvent such as isopropyl acetate, t-butyl methyl ether, ethyl acetate or toluene and evaporation of the extract to dryness.

The allyloxycarbonyl protective group is removed by hydrogenolysis by treating the compound with a catalytic amount of $(Ph_3P)_4Pd(O)$ in methanol or ethanol and sodium borohydride (about 2 mols/mole of allyloxycarbonyl compound) at about 0° to 10° C. Where the $R^1$ protective group is TBDMS, the hydrogenolysis is omitted and it and the 7-O-trimethylsilyl group are eliminated by treatment with a strong acid at about pH 3 as follows. After about 0.5 to 2 hours the mixture is acidified to about pH 3 with a strong acid such as hydrochloric acid, sulfuric acid or methanesulfonic acid; aged at about 15°–25° C. for about 2 to 6 hours; diluted with water; washed with ethyl acetate/hexanes; basified with a bicarbonate; and extracted with an organic solvent such as i-propyl acetate. The extract is evaporated to dryness. A solution of the residue in acetonitrile on treatment with benzoic acid provides the corresponding benzoic acid salts.

The utility and methods of use of the compounds produced by the novel process of this invention are well known by those skilled in the art and fully described in the scientific and patent literature such as EP 0465121.

They have significant parasiticidal activity as anthelmintics, ectoparasiticides, insecticides and acaricides, in human and animal health and in agriculture. As agricultural pesticides, they have activity against insect pests of stored grains such as Tribolium sp., Tenebrio sp., and of agricultural plants such as spider mites (Tetranychus sp.), aphids (Acyrthiosiphon sp.); against migratory orthopterans such as locusts and immature stages of insects living on plant tissue. The compounds are useful as nematocides for the control of soil nematodes and plant parasites such as Meloidogyne sp. which is of importance in agriculture. The compounds are active against other plant pests such as the southern army worm and Mexican bean beetle larvae.

The compounds are applied using known techniques as sprays, dusts, emulsions and the like, to the growing or stored crops to effect protection from such agricultural pests. For the treatment of growing crops, the compound is administered at a rate of about 5–50 gms per hectare. For the protection of stored crops it is normally administered by spraying with a solution containing from 0.1–10 ppm. of the compound.

The 4"-epi-amino-4"-deoxyavermectin $B_1$ also has utility as an intermediate for N-derivatized compounds such as the N-acyl, especially N-acetyl compound which has shown interesting anthelmintic activity.

EXPERIMENTAL SECTION

GENERAL. HPLC analyses were performed using a Spectra-Physics SP8700 ternary solvent delivery system, a Vydac C18 Protein/Peptide Column (5 mm particle size, 4.6×150 mm) reverse phase column, solvent system A:B (acetonitrile:water, with 0.1 v % TFA in each) at 25° C., 3.0 mL/min, with UV detection at 245 nm. Samples of each product were isolated and purified by column chromatography (E. Merck Silica Gel 60, 230–400 mesh ASTM using ethyl acetate:hexanes mixtures) for characterization. All reactions were carried out under an atmosphere of $N_2$, and the following solvents and reagents were dried (where needed) over 3Å A or 4Å molecular sieves prior to use: MTBE, THF, EtOH, i-PrOAc, TEA, TMEDA, DMSO and MeOH. Other solvents and reagents were used as received. Karl Fisher water analyses of reaction mixtures and solvents were carded out on a Metrohm 684 KF Coulometer and were generally in the 50–100 μ/mL range. Infrared spectra were recorded on a Perkin-Elmer 1420 Ratio Recording Infrared Spectrophotometer. Melting points were determined using a DuPont 9900 DSC (2° C./rain, under $N_2$ in an open cup) and are reported as a range from the DSC extrapolated onset temperature to the peak temperature. Proton and carbon-13 spectra were recorded in $CDCl_3$ on a Bruker AM-400 at a frequency of 400.13 and 100.16 MHz, resp. The chemical shifts are reported in ppm relative to residual $CHCl_3$ for proton ($\delta = 7.27$ ppm) and $CDCl_3$ for carbon ($\delta = 77.0$ ppm). All coupling constants are reported in Hz and the following proton multiplicites are abbreviated as follows: s=singlet, d=doublet, t=triplet, q=quartet, m=mulitiplet, om=overlapping multiplets, br=broad. High resolution mass spectroscopy studies were performed in the FAB mode. Avermectin $B_1$ was used as the mixture of $B_{1a}$ and $B_{1b}$ components available as 'Abamectin'.

EXAMPLE 1

4''-epi-Amino-4''-deoxyavermectin $B_1$ Benzoate

Step A: Preparation Of 5-O-allyloxycarbonylavermectin $B_1$

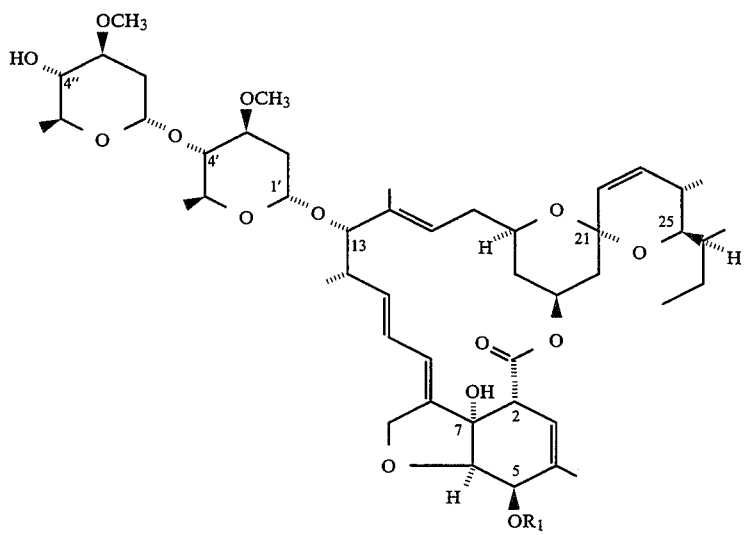

$R_1 = CO_2CH_2CH=CH_2$

Allyl chloroformate (5.50 mL, 51.6 mmol) in MTBE (15 mL) was added dropwise over 20 min to a solution of avermectin $B_1$ (3) (39.1 g, 44.9 mmol) and TMEDA (5.20 g, 44.9 mmol) in MTBE (200 mL) at $-15°$ C. to give a white precipitate. The reaction mixture was aged for 1.5 h at $-10°$ to $-15°$ C., then poured into 2% aq $H_3PO_4$ (125 mL). The organic phase was separated and evaporated in vacuo to give a solid white foam (52.4 g). HPLC assay: gradient, solvent A:B=65:35 to 75:25 over 15 min; results: ($B_{1b}$: $t_R$=6.1 min. 3.5 g, 3.7 mmol; $B_{1a}$: $t_R$=7.8 min; 38.3 g, 40.0 mmol); yield=97% (vs. a wt % standard).

$^1$H NMR: $\delta$5.94 (ddt, J=17.1, 10.4, 5.8, C$\beta$H), 5.85 (m, $H_9$), 5.78–5.71 (om, $H_{10}$, $H_{11}$, $H_{23}$), 5.57 (br s, $H_3$), 5.55 (dd, J=10.0, 2.7, $H_{22}$), 5.42–5.34 (om, $H_5$, $H_{19}$, $H_{1''}$, $C_\gamma ZH$), 5.27 (m, $C_{\gamma E}H$), 4.99 (m, $H_{15}$), 4.77 (d, J=3.0,$H_{1'}$), 4.70–4.66 (om, $C_{8a}H$, $C_\alpha H_2$), 4.61 (dd, J=14.3, 2.1, $C_{8a}H$), 4.12 (d, J=6.0, $H_6$), 3.99 (s, 7-OH), 3.93 (br s, $H_{13}$), 3.88–3.80 (om, $H_{17}$, $H_5'$), 3.77 (dq, J=9.4, 6.3, $H_5''$), 3.62 (m, $H_3'$), 3.51–3.45 (om, $H_3''$, $H_{25}$), 3.43, 3.42 (s, 3'-OCH$_3$, s, 3''-OCH$_3$), 3.37 (q, J=2.3, $H_2$), 3.24 (t, J=9.0, $H_4'$), 3.16 (br t, J=9.2, $H_4''$), 2.58 (d, J=1.5, 4''-OH), 2.52 (m, $H_{12}$), 2.35–2.20 (om, $C_{16}H_2$, $H_{24}$, $C_{2'}H_{eq}$, $C_{2''}H_{eq}$), 2.02 (dd, J=7.4, 1.4, $C_{20}H_{eq}$), 1.81 (br s, $C_{4a}H_3$), 1.81–1.76 (om, $C_{18}H_{eq}$), 1.62–1.45 (om, $C_{2'}H_{ax}$, $C_{2'}H_{ax}$, $C2''H_{ax}$, $H_{26}$, $C_{27}H_2$), 1.49 (s, $C_{14a}H_3$), 1.27 (d, J=6.3, $C_{6''}H3$), 1.25 (d, J=6.3, $C_{6'}H3$), 1.16 (d, J=6.9, $C_{12a}H_3$), 0.96–0.87 (om, $C_{24a}H_3$, $C_{26a}H_3$, $C_{28}H_3$, $C_{18}H_{ax}$).

$^{13}$C NMR: $\delta$173.5 ($C_1$), 154.9 (OCO$_2$), 139.3 ($C_8$), 138.1 ($C_{11}$), 136.3 ($C_{23}$), 135.2 ($C_{14}$), 133.1 ($C_4$), 131.5 ($C_\beta$), 127.8 ($C_{22}$), 124.8 ($C_{10}$), 121.6 ($C_3$), 120.4 ($C_9$), 118.7 ($C_\gamma$), 118.3 ($C_{15}$), 98.5 ($C_{1''}$), 95.8 ($C_{21}$), 94.9 ($C_{1'}$), 81.9 ($C_{13}$), 80.9 ($C_7$), 80.4 ($C_{4'}$), 79.4 ($C_{3'}$), 78.2 ($C_{3''}$), 77.5 ($C_6$), 76.1 ($C_4$), 74.9 ($C_{25}$), 73.6 ($C_5$), 68.8 ($C_\alpha$), 68.6 ($C_{19}$), 68.5 ($C_{8a}$), 68.4 ($C_{17}$), 68.1 ($C_{5''}$), 67.3 ($C_{5'}$), 56.5, 56.4 (3'-OCH$_3$, 3''-OCH$_3$), 45.8 ($C_2$), 40.5 ($C_{20}$), 39.8 ($C_{12}$), 36.6 ($C_{18}$), 35.2 ($C_{26}$), 34.5 ($C_{2'}$), 34.2$_6$ ($C_{16}$), 34.2$_3$ ($C_{2''}$), 30.6 ($C_{24}$), 27.5 ($C_{27}$), 20.2 ($C_{12a}$), 19.7 ($C_{4a}$), 18.4 ($C_{6'}$), 17.7 ($C_{6''}$), 16.4 ($C_{24a}$), 15.1 ($C_{14a}$), 13.0 ($C_{26a}$), 12.1 ($C_{28}$).

IR (CCl$_4$) $\lambda_{max}$: 3500, 3480, 1745, 1715, 1460, 1370, 1290, 1260, 1160, 1100, 1065, 990 cm$^{-1}$. HRMS: $[M+Li]^+$=963.5302 (calculated=963.5292).

Step B: Preparation of 4''-oxo-5-O-allyloxycarbonyl avermectin B₁

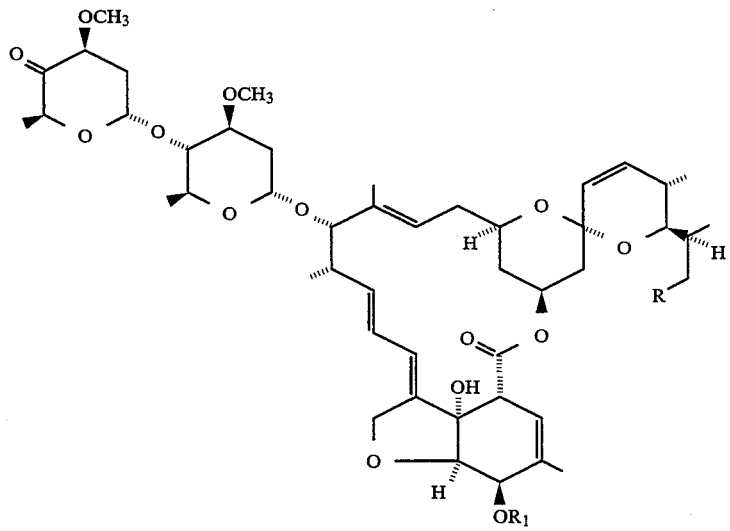

R₁ = CO₂CH₂CH=CH₂

A solution of PhOPOCl₂ (7.7 mL, 52.0 mmol) in i-PrOAc (15 mL) was added dropwise over 1 h to a solution of 5-O-AOC AVM B₁ from Step A (29.7 g, 30.6 mmol by assay), DMSO (8.7 mL, 122 mmol) and TEA (21.3 mL, 153 mmol) in i-PrOAc (160 mL) at −15° C. The mixture was aged for 1 h at −15° C., then poured into 1% aq H₃PO₄. The aqueous phase was extracted with i-PrOAc (3×50 mL), and the combined organic phases were washed with sat aq NaHCO₃ (50 mL) and evaporated in vacuo to a yellowish solid (37.6 g). HPLC assay: sample preparation, 40.0 mg of crude ketone in 0.5 mL EtOH was treated with 4 mg of NaBH₄ for 2 min to give a mixture of C₄'''-OH epimers, then diluted to 100 mL with acetonitrile; gradient, solvent A:B=65:35 to 75:25 over 15 min; results: (4''-epi-OH B₁ᵦ: $t_R$=5.4 min; 1.77 g, 1.87 mmol; B₁ₐ: $t_R$=6.80 min, 19.2 g, 20.1 mmol; 4''-OH B₁ᵦ: $t_R$=6.0 min, 0.42 g, 0.44 mmol; B₁ₐ: $t_R$=7.8 min, 4.99 g, 5.2 mmol; total=27.6 mmol); assay yield=90% (vs. a wt % standard).

¹H NMR: δ 5.94 (ddt, J=17.1, 10.4, 5.6, $C_\beta H$), 5.86 (m, H₉), 5.78-5.72 (om, H₁₀, H₁₁, H₂₃), 5.57-5.53 (om, H₃, H₂₂), 5.40-5.34 (om, H₅, H₁₉, H₁''', $C_\gamma zH$), 5.26 (m, C₆₅ₑH), 5.00 (m, H₁₅), 4.80 (br d, J=2.8, H₁'), 4.70-4.65 (om, C₈ₐH, C₆₀ H₂), 4.61 (dd, J=14.2, 2.0, C₈ₐH), 4.42 (q, J=6.6, H₅''), 4.20 (dd, J=11.7, 6.4, H₃''), 4.12 (d, J=6.1, H₆), 4.00 (s, 7-OH), 3.94 (br s, H₁₃), 3.93-3.83 (om, H₁₇, H₅'), 3.68 (m, H₃'), 3.51 (s, 3''-OCH₃), 3.49 (dd, J=10.1, 1.3, H₂₅), 3.45 (s, 3'-OCH₃), 3.38 (q, J=2.2, H₂), 3.33 (t, J=8.8, H₄'), 2.58 (ddd, J=12.8, 6.4, 1.8, C₂''H_{eq}), 2.53 (m, H₁₂), 2.32-2.23 (om, C₁₆H₂, H₂₄, C₂'H_{eq}), 2.13 (m, C₂''H_{ax}), 2.02 (dd, J=9.2, 2.9, C₂₀H_{eq}), 1.82 (br s, C₄ₐH₃), 1.81-1.76 (om, C₁₈H_{eq}), 1.64-1.46 (om, C₂₀H_{ax}, C₂'H_{ax}, H₂₆, C₂₇H₂), 1.50 (s, C₁₄ₐH₃), 1.28 (d, J=6.6, C₆''H₃), 1.27 (d, J=6.2, C₆'H₃), 1.17 (d, J=6.9, C₁₂ₐH₃), 0.97-0.91 (om, C₂₄ₐH₃, C₂₆ₐH₃, C₂₈H₃), 0.88 (m, C₁₈H_{ax}).

¹³C NMR: δ205.9, 173.5, 154.9, 139.4, 137.9, 136.3, 135.1, 133.2, 131.5, 127.8, 124.9, 121.5, 120.4, 118.7, 118.4, 98.1, 95.8, 95.0, 82.1, 81.3, 80.9, 79.2, 78.1, 77.5, 74.9, 73.6, 70.8, 68.8, 68.53, 68.50, 68.4, 67.0, 58.3, 56.5, 45.8, 40.9, 39.7, 39.5, 36.6, 35.2, 34.6, 34.3, 30.6, 27.5, 20.3, 19.7, 18.4, 16.4, 15.1, 13.9, 13.0, 12.1.

IR (CCl₄) $\lambda_{max}$: 3460, 2990, 2940, 1750, 1718, 1455, 1375, 1270, 1205, 1165, 1130, 1060, 990 cm⁻¹.

HRMS: [M+Li]⁺=961.5144 (calculated=961.5136).

Step C: Preparation of 4″-epi-Amino-5-O-allyloxycarbonyl-4″-deoxyavermectin $B_1$ 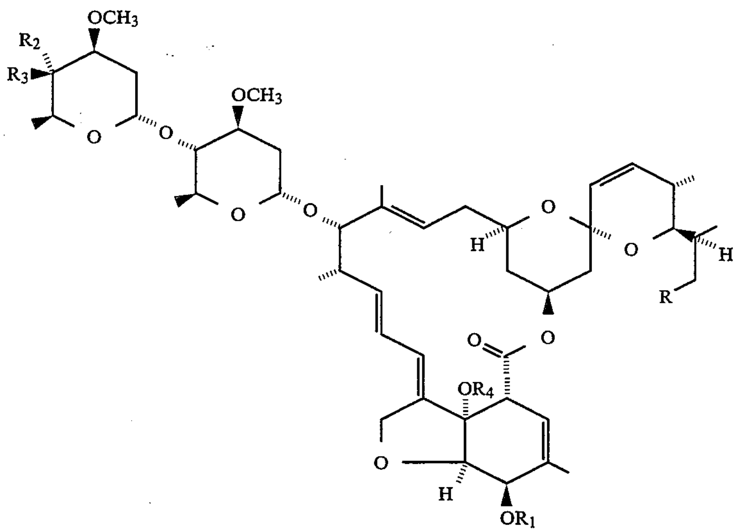 IIa: $R_2$ = H, $R_3$ = $NH_2$, $R_1$ = $CO_2CH_2CH{=}CH_2$, $R_4$ = H
IIb: $R_2$ = H, $R_3$ = $NH_2$, $R_1$ = $CO_2CH_2CH{=}CH_2$, $R_4$ = TMS A mixture of crude ketone from Step B (26.3 g, 27.5 mmol by assay), hexamethyldisilazane (15.3 g, 94.7 mmol) and $ZnCl_2$ (4.16 g, 30.5 mmol) in i-PrOAc (135 mL) was warmed to 50° C., aged for 4 h, then cooled to 5° C. $NaBH_4$ (3.25 g, 85.9 mmol) and EtOH (50 mL) were added, while maintaining the temperature at $<10°$ C., and the mixture was aged for 1 h at 20° C. The mixture was treated dropwise with 10% aq acetic acid (100 mL) and aged for 15 min. The pH of the mixture was adjusted to 8.0 with 5N aq NaOH and the precipitated zinc salts were filtered. The aqueous phase was extracted with i-PrOAc (3×50 mL), and the combined organic phases were evaporated in vacuo to give IIa,b as a yellowish solid (37.2 g). HPLC assay: gradient, solvent A:B=50:50 to 85:15 over 20 min; results: (IIa) ($t_R$: $B_{1b}$=7.0 min, $B_{1a}$=8.0 min; 14.7 g, 15.4 mmol); (IIb) ($t_R$: $B_{1b}$=1.6 min; $B_{1a}$=12.0 min; 7.9 g, 7.7 mmol); (IIf) ($t_R$: $B_{1b}$=2.7 min; $B_{1a}$=3.1 min; 0.5 g, 0.6 mmol); (IIc) ($t_R$: $B_{1b}$=7.4 min; $B_{1a}$=8.8 min; 1.1 g, 1.2 mmol); assay yield=86% (vs. a wt % standard).

(IIa): $^1$H NMR: δ 5.94 (ddt, J=17.2, 10.5, 5.8, $C_\beta H$), 5.85 (m, $H_9$), 5.77–5.01 (om, $H_{10}$, $H_{11}$, $H_{23}$), 5.57 (br s, $H_3$), 5.54 (dd, J=9.9, 2.6, $H_{22}$), 5.42–5.34 (om, $H_5$, $H_{19}$, $H_{1''}$, $C_{65\,Z}H$), 5.26 (m, $C_{\gamma E}H$), 4.98 (m, $H_{15}$), 4.77 (d, J=3.1, $H_{1'}$), 4.70–4.58 (om, $C_{8a}H_2$, $C_{60}$ $H_2$), 4.12 (d, J=6.1, $H_6$), 4.00 (br q, J=6.3, $H_{5''}$), 3.93 (br s, $H_{13}$), 3.88–3.80 (om, $H_{17}$, $H_{5'}$), 3.63–3.55 (om, $H_{3'}$, $H_{3''}$), 3.48 (dd, J=9.8, 1.1, $H_{25}$), 3.43, 3.37 (s, 3′-$OCH_3$, s, 3″-$OCH_3$), 3.37 (om, $H_2$), 3.22 (t, J=9.0, $H_{4'}$), 3.05 (br d, J=2.0, $H_{4''}$), 2.51 (m, $H_{12}$), 2.35–2.16 (om, $C_{16}H_2$, $H_{24}$, $H_{26}$, $C_{2'}H_{eq}$), 2.02 (m, $C_{20}H_{eq}$), 1.92 (dd, J=13.0, 5.0, $C_{2''}H_{eq}$), 1.81 (br s, $C_{4a}H_3$), 1.80–1.75 (om, $C_{18}H_{ax}$), 1.62–1.41 (om, $C_{20}H_{eq}$, $C_{27}H_2$, $C_{2'}H_{ax}$, $C_{2''}H_{ax}$), 1.49 (s, $C_{14a}H_3$), 1.24 (od's, J~6.3, $C_{6''}H_3$, $C_{6'}H_3$), 1.15 (d, J=6.9, $C_{12a}H_3$), 0.96'0.83 (om, $C_{18}H_{ax}$, $C_{24a}H_3$, $C_{26a}H_3$, $C_{28}H_3$).

$^{13}$C NMR: δ 173.4, 154.8, 139.3, 138.0, 136.3, 135.2, 133.1, 131.5, 127.8, 124.8, 121.6, 120.4, 118.7, 118.3, 98.7, 95.8, 95.0, 82.0, 80.9, 80.6, 79.4, 77.5, 75.2, 74.9, 73.6, 68.8, 68.54, 68.49, 68.37, 67.3, 66.1, 56.7, 55.3, 50.9, 45.8, 40.5, 39.8, 36.6, 35.2, 34.3, 30.6, 27.5, 20.2, 19.7, 18.3, 17.3, 16.4, 15.1, 13.0, 21.1. IR ($CCl_4$) λmax: 3500, 2990, 2930, 1745, 1715, 1450, 1370, 1240, 1160, 1110, 990 $cm^{-1}$. HRMS: $[M+Li]^+$=962.5426 (calculated=962.5452)

(IIb): $^1$H NMR: δ 5.95 (ddt, J=17.3, 10.6, 5.6, $C_\beta H$), 5.77–5.61 (om, $H_3$, $H_9$, $H_{10}$, $H_{11}$, $H_{23}$), 5.52 (dd, J=2.6, 9.9, $H_{22}$), 5.40–5.35 (om, $H_{1''}$, $C_{\gamma Z}H$), 5.32 (br d, J=5.5, $H_5$), 5.27 (m, $C_{65\,E}H$), 5.11–5.01 (om, $H_{15}$, $H_{19}$), 4.80 (br d, J=3.2, $H_{1'}$), 4.67 (m, $C_\alpha H_2$), 4.62 (om, $C_{8a}H_2$), 4.17 (d, J=6.0, $H_6$), 4.03–3.81 (om, $H_{5'}$, $H_{5''}$, $H_{13}$, $H_{17}$), 3.67–3.56 (om, $H_{3'}$, $H_{3''}$), 3.46 (br d, J=10.0, $H_{25}$), 3.42, 3.37 (s, $C_{3'}$-$OCH_3$, $C_{3''}$-$OCH_3$), 3.25 (om, $H_2$, $H_{4'}$), 3.08 (m, $H_{4''}$), 2.56 (m, $H_{12}$), 2.35–2.18 (om, $C_{16}H_2$, $C_{20}H_{eq}$, $H_{24}$, $C_{2'}H_{eq}$), 1.96–1.76 (om, $C_{18}H_{eq}$, $C_{2''}H_2$), 1.80 (s, $C_{4a}H_3$), 1.70–1.38 (om, $H_{26}$, $C_{27}H_2$, $C_{2'}H_{ax}$), 1.51 (s, $C_{14a}H_3$), 1.34–1.24 (om, $C_{20}H_{ax}$, $C_{6''}H_3$, $C_{6'}H_3$), 1.19 (d, J=7.0, $C_{12a}H_3$), 0.97–0.82 (om, $C_{18}H_{ax}$, $C_{24a}H_3$, $C_{26a}H_3$, $C_{28}H_3$), 0.15 (s, OTMS).

$^{13}$C NMR: δ169.9, 155.1, 139.4, 137.2, 136.0, 135.1, 131.5, 130.0, 128.1, 125.00, 124.97, 121.6, 118.7, 118.6, 98.6, 95.8, 95.1, 84.5, 82.0, 80.4, 79.2, 77.6, 75.1, 74.9, 73.8, 68.7, 68.3, 68.0, 67.8, 67.2, 66.0, 56.5, 55.3, 50.9, 47.1, 40.9, 40.0, 36.3, 35.3, 34.5, 34.2, 30.5, 29.8, 27.5, 20.2, 19.7, 18.3, 17.4, 16.4, 15.1, 13.0, 12.1, 2.1.

IR ($CCl_4$)$\lambda_{max}$: 3400, 2990, 2940, 1740, 1450, 1370, 1305, 1255, 1160, 1110, 990 $cm^{-1}$.

HRMS: $[MH]^+$=1028.5784 (calculated=1028.5766).

Step D: Preparation of 4"-epi-amino-4"-deoxyavermectin B₁ Benzoate

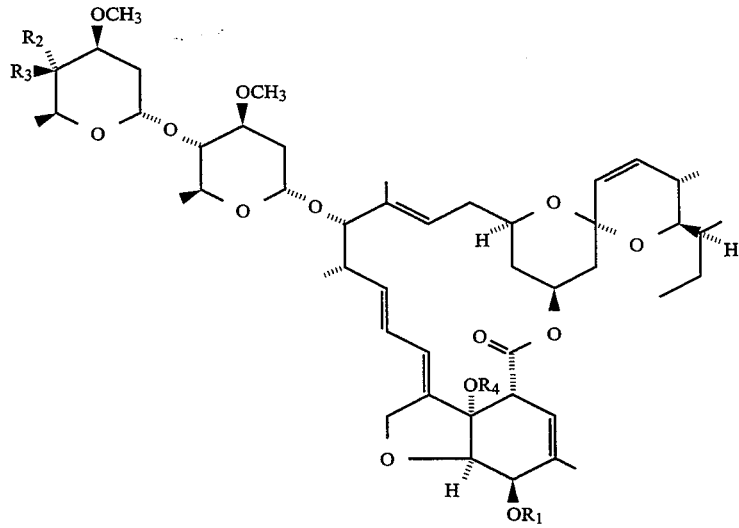

$R_1 = R_2 = R_4 = H$; $R_3 = NH_3O_2CPh$
IIf(benzoate)

A mixture of crude 4"-epi-amino-avermectins IIa,b (28.4 mmol) and $(Ph_3P)_4Pd(0)$ (33 mg, 0.028 mmol) in EtOH (150 mL) at 5° C was treated portionwise with $NaBH_4$ (2.15 g, 56.8 retool). The mixture was aged for 1 h at 5° C. then 12N aq HCl (11 mL) was added dropwise to destroy excess borohydride and to acidify (pH=2.5–3.0) the solution. This mixture was aged for 4 hr at 20° C., diluted with $H_2O$ (200 mL), washed with a mixture of ethyl acetate:hexanes (1:1; 4×50 mL), made basic with sat aq $NaHCO_3$ (300 mL) and extracted with i-PrOAc (4×75 mL). The combined extracts were evaporated in vacuo to give IIf as a solid foam weighing 30.1 g. HPLC assay: gradient, solvent, A:B=40:60 to 60:40 over 15 min; results: IIf ($B_{1b}$: $t_R$=6.1 min; 1.7 g, 3.5 mmol; $B_{1a}$: $t_R$=7.4 min; 18.8 g, 21.6 mmol); yield=88.4%. A sample of crude IIf (20 g) was filtered through silica gel 60 (20 g), eluting with ethyl acetate to give 11.3 g of purified product. A solution of IIf (11.3 g, 12.9 mmol) in acetonitrile (45 mL) was treated with benzoic acid (1.72 g, 14.1 mmol) then aged 1 h at 20° C. and 1 h at 0° C. to give 4"-epi-amino-4"-deoxyavermectin B₁ benzoate (15.1 g) after filtration, washing and drying in vacuo (40° C., 100 mm Hg), m.p.=145.4–148.7° C.

¹H NMR: δ 8.08 (m, $H_{2'''}$, $H_{6'''}$), 7.53 (m, $H_{4'''}$), 7.43 (m, $H_{3'''}$, $H_{5'''}$), 5.87 (m, $H_9$), 5.76 (dd, J=9.9, 1.5, $H_{23}$), 5.74–5.71 (om, $H_{10}$, $H_1$), 5.55 (dd, J=9.9, 2.5, $H_{22}$), 5.42–5.36 (om, $H_3$, $H_{19}$, $H_{1''}$), 5.00 (m, $H_{15}$), 4.85 (br s, active H), 4.77 (br d, J=3.0, $H_{1'}$), 4.68 (m, $C_{8a}H_2$), 4.30 (br d, J=6.1, $H$), 4.07 (br q, J=6.7, $H_{5''}$), 3.97 (d, J=6.2, $H_6$), 3.93 (br s, $H_{13}$), 3.90–3.81 (om, $C_{17}H_2$, $H_{5'}$), 3.69–3.57 (om, $H_{3'}$, $H_{3''}$), 3.48 (dd, J=9.8, 1.2, $H_{25}$), 3.4 (s, $C_{3'}$-$OCH_3$), 3.40 (s, $C_{3''}$-$OCH_3$), 3.29 (q, J=2.2, $H_2$), 3.23 (t, J=9.0, $H_{4'}$), 2.52 (m, $H_{12}$), 2.31–2.20 (om, $C_{16}H_2$, $H_{24}$, $C_{2'}H_{eq}$), 2.04–1.98 (om, $H_{20}H_{eq}$, $C_{2''}H_{eq}$), 1.87 (br s, $C_{4a}H_3$), 1.80–1.73 (m, $C_{18}H_{eq}$, $C_{2''}H_{ax}$), 1.64–1.44 (om, $H_{20}$, $H_{26}$, $C_{27}H_2$, $C_{2'}H_{ax}$), 1.49 (br s, $C_{14a}H_3$), 1.29 (d, J=6.6, $C_{6''}H_3$), 1.23 (d, J=6.2, $C_{6'}H_3$), 1.16 (d, J=6.9, $C_{12a}H_3$), 1.10 (d, J=6.8, $C_{26a}H_3$ of $B_{1b}$ isomer), 0.96–0.91 (om, $C_{24a}H_3$, $C_{26a}H_3$, $C_{28}H_3$), 0.89 (m, $C_{18}H_{ax}$).

¹³C NMR: δ 173.7 ($C_1$), 170.6 ($CO_{2-}$), 139.6 ($C_8$), 137.9 ($C_4$, $C_{11}$), 136.3 ($C_{23}$), 135.1 ($C_{14}$), 132.3 ($C_{4'''}$), 132.0 ($C_{1'''}$), 129.8 ($C_{2'''}$, $C_{6'''}$), 128.1 ($C_{3'''}$, $C_{5'''}$), 127.7 ($C_{22}$), 124.7 ($C_{10}$), 120.4 ($C_9$), 118.3 ($C_{15}$), 118.0 ($C_3$), 98.6 ($C_{1''}$), 95.8 ($C_{21}$), 95.0 ($C_{1'}$), 82.0 ($C_{13}$), 80.8 ($C_{4'}$), 80.4 ($C_7$), 79.2 ($C_{3'}$), 79.1 ($C_6$), 74.9 ($C_{25}$), 74.1 ($C_{3''}$), 68.38 ($C_{8a}$), 68.35 ($C_{19}$), 68.33 ($C_{17}$), 67.7 ($C_5$), 67.1 ($C_{5'}$), 65.1 ($C_{5''}$), 56.6 (3'-$OCH_3$), 55.5 (3"-$OCH_3$), 50.3 ($C_{4''}$), 45.7 ($C_2$), 40.5 ($C_{20}$), 39.7 ($C_{12}$), 36.6 ($C_{18}$), 35.1 ($C_{26}$), 34.5 ($C_{2'}$), 34.2 ($C_{16}$), 30.6 ($C_{24}$), 29.9 ($C_{2''}$), 27.5 ($C_{27}$), 20.2 ($C_{12a}$), 19.9 ($C_{4a}$), 18.2 ($C_{6'}$), 17.1 ($C_{6''}$), 16.4 ($C_{24a}$), 15.1 ($C_{14a}$), 12.9 ($C_{26a}$), 12.0 ($C_{28}$).

IR ($CCl_4$) $\lambda_{max}$: 3560, 3480, 2980, 2940, 1711, 1600, 1530, 1450, 1370, 1160, 1100, 980 cm$^{-1}$.

HRMS: $[M+Li]^+$ = 878.5250 (calculated = 878.5241 for free amine). Anal. Calculated for $C_{55}H_{79}NO_{15}$ (corrected for 0.8 wt % $H_2O$ content): C, 65.91; H, 8.03; N, 1.39. Found: C, 65.88; H, 8.13; N, 1.32.

EXAMPLE 2

4''-epi-Methylamino-4''-deoxyavermectin $B_1$ Benzoate

Step A: Preparation of 4''-epi-methylamino-5-O-allyloxycarbonyl-7-O-trimethylsilyl-4''-deoxyavermectin $B_1$

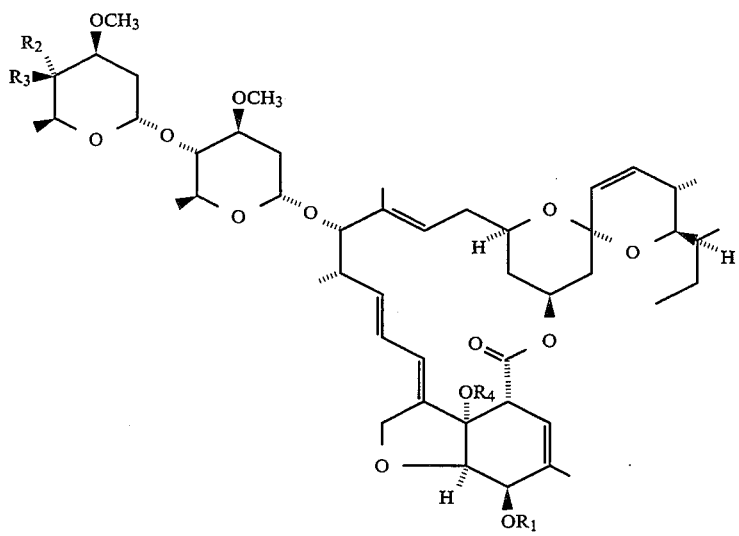

IId: $R_1$ = $CO_2CH_2CH$=$CH_2$; $R_2$ = H; $R_3$ = $CH_3NH$; $R_4$ = TMS.

A mixture of ketone from Example 1, Step B (42.4 g, 44.4 mmol), heptamethyldisilazane (31.9 g, 182 mmol) and $ZnCl_2$ (6.75 g, 49 mmol) in i-PrOAc (180 mL) was warmed to 50° C., aged for 3 h, then cooled to 5° C. $NaBH_4$ (8.4 g, 220 mmol) and EtOH (100 mL) were added, while maintaining the reaction temperature at <10° C., and aged for 1 h at 20° C. The mixture was treated with 2N aq acetic acid (200 mL), aged for 15 min. The pH of the mixture was adjusted to 8.0 with 5N aq NaOH and the precipitated zinc salts were filtered. The aqueous phase was extracted with i-PrOAc (3×50 mL,), and the combined organic phases were evaporated in vacuo to give a yellowish solid (71 g). HPLC assay: isocratic, solvent A:B=75:25; results: IId ($t_R$: $B_{1b}$=4.9 min, $B_{1a}$=5.8 min, 35.98 g, 34.6 mmol; IIe ($t_R$: $B_{1a}$=6.9 min, 2.68 g, 2.6 mmol; and 4''-epi-$CH_3NH$-7-O-TMS-4''-deoxyAVM ($t_R$: $B_{1b}$=2.5 min, $B_{1a}$=3.1min, 2.4 g, 2.5 mmol; assay yield=83.5% (vs. a wt % standard).

$^1H$ NMR: δ 5.95 (ddt, J=17.4, 10.6, 4.8, $C_\beta H$), 5.77–5.71 (om, $H_3$, $H_9$, $H_{10}$, $H_{11}$, $H_{23}$), 5.51 (dd, J=9.9, 2.6, $H_{22}$), 5.40–5.33 (om, $H_{1''}$, $C_{65}$ $_EH$), 5.31 (br d, J=6.0, $H_5$), 5.26 (m, $C_{65}$ $_EH$), 5.11–5.02 (om, $H_{15}$, $H_{19}$), 4.79 (br d, J=3.0, $H_{1'}$), 4.67 (m, $C_{60}H_2$), 4.62 (om, $C_{8a}H_2$), 4.16 (d, J=6.0, $H_6$), 3.97–3.80 (om, $H_{5'}$, $H_{5''}$, $H_{13}$, $H_{17}$), 3.80–3.58 (om, $H_{3'}$, $H_{3''}$), 3.46 (dd, J=9.9, 1.0, $H_{25}$), 3.41, 3.37 (s, $C_{3'}$-$OCH_3$, $C_{3''}$-$OCH_3$), 3.27–3.22 (om, $H_{4'}$, $H_2$), 2.66 (br d, J=3.3, $H_{4''}$), 2.57 (s, $NCH_3$), 2.56 (om, $H_{12}$), 2.32–2.03 (om, $C_{16}H_2$, $H_{24}$, $C_{2'}H_{eq}$, $C_{20}H_{eq}$), 1.94 1.76 (om, $C_{18\ Heq}$, $C_{2''}H_2$), 1.80 (s, $C_{4a}H_3$), 1.65–1.33 (om, $H_{26}$, $C_{27}H_2$, $C_{2'}H_{ax}$), 1.50 (s, $C_{14a}H_3$), 1.32 (om, $C_{20}H_{ax}$), 1.26 (d, J=6.4, $C_{6''}H_3$), 1.24 (d, J=6.0, $C_{6'}H_3$), 1.18 (d, J=7.0, $C_{12a}H_3$), 0.96–0.80 (om, $C_{18}H_{ax}$, $C_{24a}H_3$, $C_{26a}H_3$, $C_{28}H_3$), 0.15 (s, OTMS).

$^{13}C$ NMR: δ 169.9, 155.1, 139.4, 137.2, 136.0, 135.1, 131.5, 130.0, 128.1, 125.0(2C), 121.7, 118.7, 118.6, 98.5, 95.8, 95.1, 84.5, 81.9, 80.3, 79.2, 77.6, 75.5, 74.9, 73.8, 68.7, 68.3, 68.0, 67.8, 67.4, 67.2, 60.0, 56.6, 55.5, 47.1, 40.9, 40.0, 38.5, 36.3, 35.3, 34.5, 34.2, 31.1, 30.5, 27.5, 20.2, 19.7, 18.3, 18.2, 16.4, 15.1, 12.9, 12.1, 2.1.

IR $(CCl_4)\lambda_{max}$: 3400, 2980, 2940, 1735, 1450, 1375, 1305, 1255, 1165, 1110, 990 $cm^{-1}$.

HRMS: $[MH]^+$ =1042.5928 (calculated=1042.5922).

Step B: Preparation of 4″-epi-methylamino-4″-deoxyavermectin B₁ Benzoate

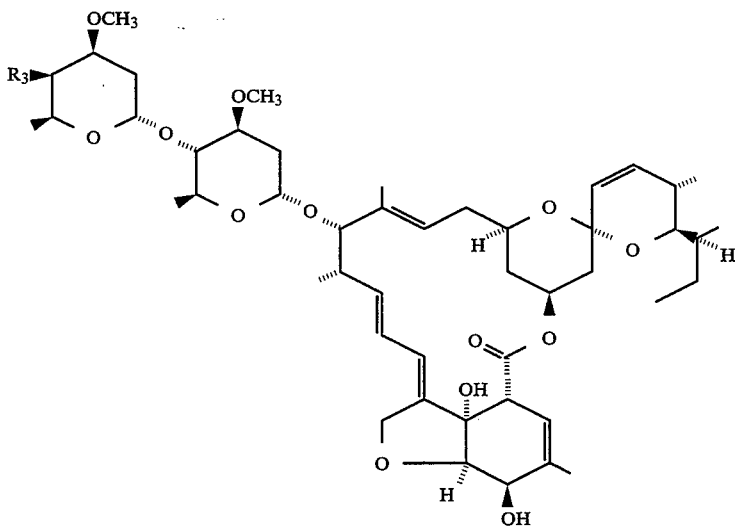

R₃ = CH₃NH.HO₂CPh
IIg(benzoate)

A solution of methylamino-avermectin IId (8.64 g, 8.29 mmol) and (Ph₃P)₄Pd(0) (5 mg, 0.004 mmol) in EtOH (40 mL) at 5° C. was treated portionwise with NaBH₄ (0.62 g, 16.4 mmol). The mixture was aged for 1 h, then 12N aq HCl (6.5 mL) was added dropwise to destroy the excess borohydride and to acidify (pH=2.5–3.0) the EtOH solution. This mixture was aged for 4 h at 20° C., diluted with H₂O (75 mL), washed with a mixture of ethyl acetate:hexanes (1:1 4=50 mL), made basic with sat aq NaHCO₃ (125 mL) and extracted with i-PrOAc (4=50 mL). The combined extracts were evaporated in vacuo to give a solid foam (10.1 g). HPLC assay: gradient, solvent A:B=50:50 to 85:15 over 20 min; results: IIg (B$_{1b}$: t$_R$=4.4 min, 0.56 g, 0.6 mmol; B$_{1a}$: t$_R$=5.64 min, 5.44 g, 6.1 mmol); assay yield=81.6% (vs. a wt % standard). A solution of IIg (5.56 g, 6.2 mmol by assay) in MTBE (20 mL) was treated with benzoic acid (0.76 g, 6.2 mmol) and then hexanes (40 mL) was added. After aging at 25° C. for 1 h, the mixture was cooled to 2° C., aged 2 h, then filtered. The crystals were washed with 50 v % MTBE in hexanes (50 mL) and dried in vacuo to give 5.7 g of IIg benzoate, m.p. (DSC at 10° C./min.)=139°–144° C.

$^1$H NMR: δ 8.10 (m, H$_{2'''}$, H$_{6'''}$), 7.53 (m, H$_{4'''}$), 7.43 (m, H$_{3'}$, H$_{5'''}$), 5.87(m, H$_9$), 5.76 (dd, J=9.8, 1.7, H$_{23}$), 5.75–5.72 (om, H$_{10}$, H$_{11}$), 5.55 (dd, J=9.8, 2.6, H$_{22}$), 5.43–5.37 (om, H$_3$, H$_{19}$, H$_{1''}$), 5.22 (v br, active H), 5.00 (m, H$_{15}$), 4.76 (br d, J=3.0, H$_{1'}$), 4.69 (m, C$_{8a}$H$_2$), 4.30 (br d, J=6.1, H$_5$), 4.03 (br q, J=6.7, H$_{5''}$), 3.98 (d, J=6.2, H$_6$), 3.94 (br s, H$_{13}$), 3.88 (m, C$_{17}$H$_2$), 3.82 (dq, J=9.1, 6.2, H$_{5'}$), 3.74 (ddd, J=11.5, 5.0, 3.8, H$_{3''}$), 3.58 (m, H$_{3'}$), 3.48 (dd, J=9.9, 1.3, H$_{25}$), 3.42 (s, C$_{3'}$-OCH$_3$), 3.40 (s, C$_{3'''}$-OCH$_3$), 3.30 (q, J=2.2, H$_2$), 3.23 (dd, J=9.1, 8.7, H$_{4'}$), 2.87 (br d, J=3.8, H$_{4''}$), 2.67 (s, N-CH$_3$), 2.52 (m, H$_{12}$), 2.31–2.25 (om, C$_{16}$H$_2$, H$_{24}$), 2.21 (dd, J=12.7, 5.0, H$_{2'eq}$), 2.05–190 (om, C$_{20}$H$_{eq}$, C$_{2''}$H$_{eq}$), 1.87 (br s, C$_{4a}$H$_3$), 1.78 (m, C$_{18}$H$_{eq}$), 1.63–1.46 (om, C$_{20}$H$_{ax}$, H$_{26}$, C$_{27}$H$_2$, C$_{2'}$H$_{ax}$, C$_{2''}$H$_{ax}$), 1.49 (br s, C$_{14a}$H$_3$), 1.34 (d, J=6.7, C$_{6''}$H$_3$), 1.23 (d, J=6.2, C$_{6'}$H$_3$), 1.16 (d, J=7.0, C$_{12a}$H$_3$), 1.11 (d, J=7.1, C$_{26a}$H$_3$ of B$_{1b}$ isomer), 0.96–0.91 (om, C$_{24a}$H$_3$, C$_{26a}$H$_3$, C$_{28}$H$_3$), 0.89 (m, C$_{18}$H$_{ax}$).

$^{13}$C NMR: δ 173.7 (C$_1$), 170.9 (CO$_{2-}$), 139.6 (C$_8$), 138.0 (C$_{11}$), 137.9 (C$_4$), 136.3 (C$_{23}$), 135.1 (C$_{14}$), 132.2 (C$_{4'''}$), 132.1 (C$_{1'''}$), 129.9 (C$_{2'''}$, C$_{6'''}$), 128.1 (C$_{3'''}$, C$_{5'''}$), 127.7 (C$_{22}$), 124.7 (C$_{10}$), 120.4 (C$_9$), 118.3 (C$_{15}$), 118.0 (C$_3$), 98.5 (C$_{1''}$), 95.7 (C$_{21}$), 95.0 (C$_1$), 81.9 (C$_{13}$), 80.8 (C$_{4'}$), 80.4 (C$_7$), 79.2 (C$_{3'}$), 79.1 (C$_6$), 74.9 (C$_{25}$), 74.8 (C$_{3''}$), 68.42 (C$_{8a}$), 68.36 (C$_{19}$), 68.33 (C$_{17}$), 67.7 (C$_5$), 67.2 (C$_{5'}$), 66.6 (C$_5$), 59.9 (C$_{4''}$), 56.6 (3'-OCH$_3$), 55.6 (3''-OCH$_3$), 45.7 (C$_2$), 40.5 (C$_{20}$), 39.7 (C$_{12}$), 37.1 (N-CH$_3$), 36.6 (C$_{18}$), 35.1 (C$_{26}$), 34.5 (C$_{2'}$), 34.2 (C$_{16}$), 30.9 (C$_{2''}$), 30.6 (C$_{24}$), 27.5 (C$_{27}$), 20.1 (C$_{12a}$), 19.9 (C$_{4a}$), 18.2 (C$_{6'}$), 17.9 (C$_{6''}$), 16.4 (C$_{24a}$), 15.1 (C$_{14a}$), 12.9 (C$_{26a}$), 12.0 (C$_{28}$).

IR (CCl$_4$) λ$_{max}$: 3595, 3460, 2995, 2940, 1715, 1455, 1380, 1160, 1120, 990 cm$^{-1}$.

HRMS: [MH]$^+$=886.5316 (calculated=886.5316) for free amine.

Anal. Calcd for C$_{56}$H$_{81}$NO$_{15}$: C, 66.71; H, 8.10; N, 1.39. Found: C, 66.96; H, 7.82; N, 1.45.

EXAMPLE 3

4″-epi-Acetylamino-4″-deoxyavermectin B₁

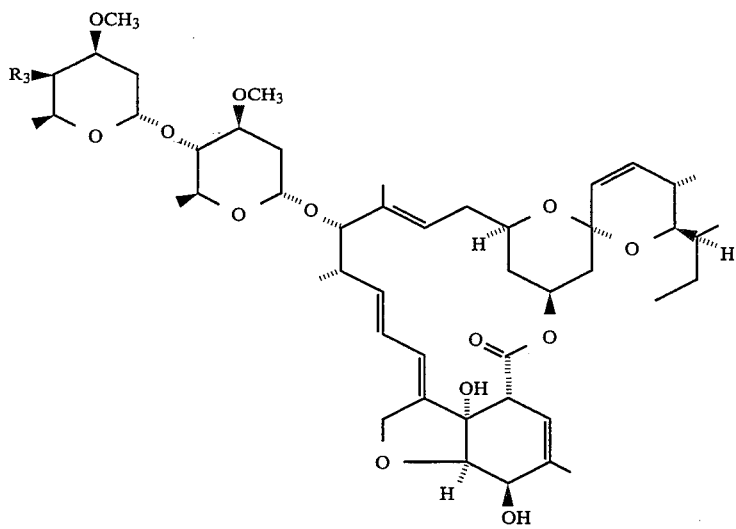

R₃ = CH₃CONH—

A solution of aminoavermectin IIf (9.24 g, 10.6 mmol by assay) in i-PrOAc (45 mL) was cooled to 5° C. and acetic anhydride (1.4 g, 13.8 mmol) was added over 5 min. The mixture was aged for 1 h then poured into sat aq NaHCO₃ (25 mL). The i-PrOAc layer was concentrated in vacuo to a yellowish solid (14.4 g) which was then dissolved into acetonitrile (35 mL) at reflux under N₂ and crystallized by slow cooling to 2° C. over a 2 h period. The slurry was aged for 1 h then filtered. The product was washed with cold (2° C.) acetonitrile (20 mL). The resulting cake was dried in vacuo at 50° C. to give 8.00 g (82% yield) of amide as a crystalline solid; m.p.=163.3°–165.7° C. HPLC assay: gradient, solvent A:B=45:55 to 65:35 over 15 min results: 2 ($B_{1b}$: $t_R$=8.8 min; $B_{1a}$: $t_R$=10.8 min).

$^1$H NMR: δ 5.86 (m, $H_9$), 5.84–5.70 (om, $H_{10}$, $H_{11}$, $H_{23}$), 5.59 (d, J=10.0, 4″-NH), 5.55 (dd, J=9.9, 2.5, $H_{22}$), 5.43–5.38 (om, $H_3$, $H_{19}$, $H_{1''}$), 4.98 (m, $H_{15}$), 4.77 (d, J=3.2, $H_{1'}$), 4.73–4.65 (m, $C_{8a}H_2$), 4.44 (dd, J=10.0, 3.2, $H_{4''}$), 4.30 (br t, J~5, $H_5$), 4.06 (dq, J=6.6, 3.2, $H_{5''}$), 4.03 (s, 7-OH), 3.97 (d, J=6.3, $H_6$), 3.93 (br s, $H_{13}$), 3.87–3.82 (om, $H_{17}$, $H_{5''}$), 3.71–3.58 (om, $H_{3'}$, $H_{3''}$,), 3.49 (dd, J=10.0, 1.3, $H_{25}$), 3.44 (s,3′-OCH₃), 3.40 (s, 3′-OCH₃), 3.30 (q, J=2.2, $H_2$), 3.21 (t, J=9.0, $H_{4'}$), 2.52 (m, $H_{12}$), 2.39 (br d, J~7, 5-OH), 2.31–2.21 (om, $C_{16}H_2$, $H_{24}$, $C_{2'}H_{eq}$), 2.07 (s, CH₃CO), 2.05–2.00 (om, $C_{20}H_{eq}$, $C_{2''}H_{eq}$), 1.87 (br s, $C_{4a}H_3$), 1.77 (m, $C_{18}H_{eq}$), 1.64–1.45 (om, $C_{20}H_{ax}$, $H_{26}$, $C_{27}H_2$, $C_{2'}H_{ax}$, $C_{2''}H_{ax}$), 1.49 (br s, $C_{14a}H_3$), 1.24 (d, J=6.2, $C_{6'}H_3$), 1.16 (d, J=6.9, $C_{12a}H_3$), 1.13 (d, J=6.6, $C_{6''}H_3$), 0.98–0.90 (om, $C_{24a}H_3$, $C_{26a}H_3$, $C_{28}H_3$), 0.89 (m, $C_{18}H_{ax}$).

$^{13}$C NMR: δ 173.8 ($C_1$), 170.7 (CH₃CO), 139.7 ($C_8$), 138.0₂ ($C_4$), 137.9₇ ($C_{11}$), 136.3 ($C_{23}$), 135.1 ($C_{14}$), 127.7 ($C_{22}$), 124.8 ($C_{10}$), 120.4 ($C_9$), 118.3 ($C_{15}$), 118.0 ($C_3$), 98.7 ($C_{1''}$), 95.8 ($C_{21}$), 95.0 ($C_{1'}$), 82.0 ($C_{13}$), 81.1 ($C_{4'}$), 80.4 ($C_7$), 79.3 ($C_{3'}$), 79.1 ($C_6$), 74.9 ($C_{25}$), 73.3 ($C_{3''}$), 68.5 ($C_{8a}$), 68.4 ($C_{5'}$, $C_{19}$), 67.7 ($C_5$), 67.1 ($C_{17}$), 65.5 ($C_{5''}$), 56.7 (3′-OCH₃), 56.1 (3″-OCH₃), 48.4 ($C_{4''}$), 45.7 ($C_2$), 40.5 ($C_{20}$), 39.8 ($C_{12}$), 36.7 ($C_{18}$), 35.2 ($C_{26}$), 34.5 ($C_{2'}$), 34.3 ($C_{16}$), 31.9 ($C_{2''}$), 30.6 ($C_{24}$), 27.5 ($C_{27}$), 23.6 (CH₃CO), 20.3 ($C_{12a}$), 20.0 ($C_{4a}$), 18.3 ($C_{6'}$), 17.1 ($C_{6''}$), 16.4 ($C_{24a}$), 15.2 ($C_{14a}$), 13.0 ($C_{26a}$), 12.1 ($C_{28}$).

IR (CCl₄)λ$_{max}$: 3590, 3480, 2990, 2940, 1712, 1685, 1510, 1450, 1380, 1150, 1130, 990 cm$^{-1}$.

HRMS: [M+Li]$^+$=920.5349 (calculated=920.5347). Anal. Calcd for $C_{50}H_{75}NO_{14}$: C, 65.70; H, 8.27; N, 1.52. Found: C, 65.79; H, 7.96; N, 1.46.

What is claimed is:

1. A process for the preparation of a compound of structural formula II

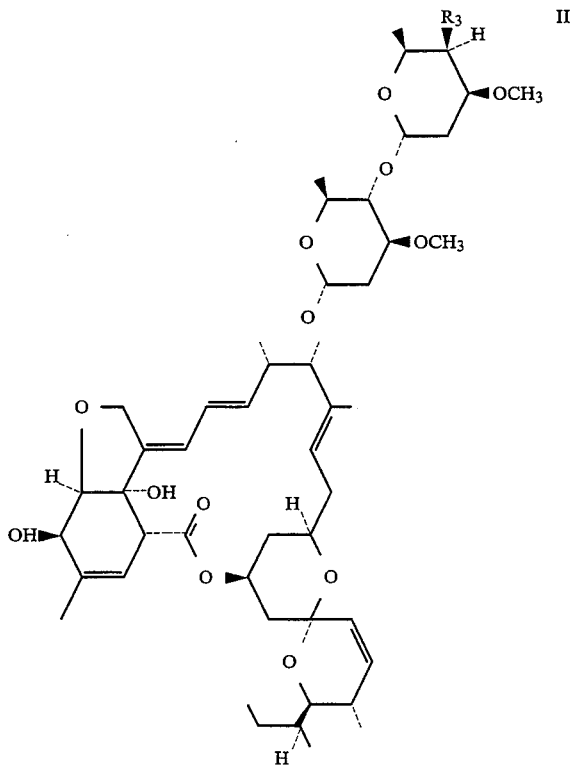

wherein $R^3$ is —NHR$^5$, wherein R$^5$ is —H or —CH₃ which comprises the steps of:

a) treating a compound of structural formula I

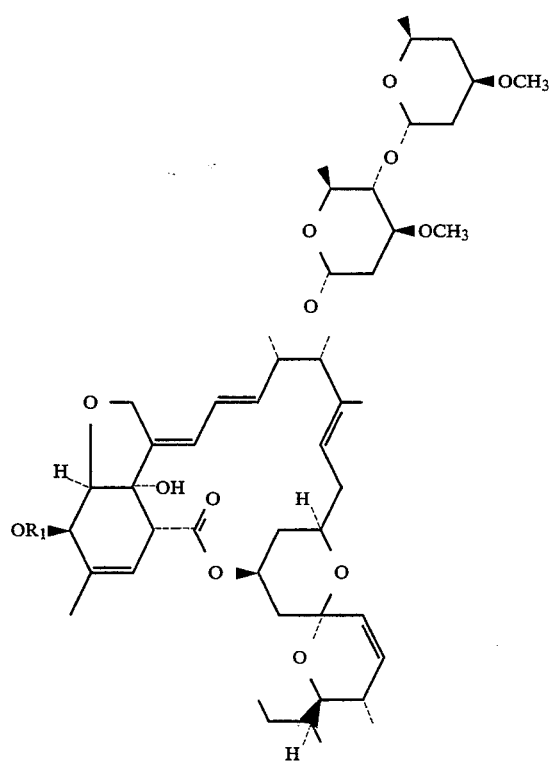

wherein $R_1 = CO_2CH_2CH=CH_2$ or $Si(CH_3)_2C(CH_3)_3$ with a compound of structural formula

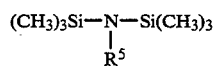

wherein $R^5$ is —H or —$CH_3$; and a Lewis acid selected from $ZnCl_2$, $ZnBr_2$ and $Zn(OCOCF_3)_2$ in an organic solvent selected from isopropylacetate, THF and toluene at a temperature of about 40° to 60° C.;

b) adding $NaBH_4$ in ethanol, while keeping the temperature below 10° C. during addition, to produce the compound of structural formula II a/d;

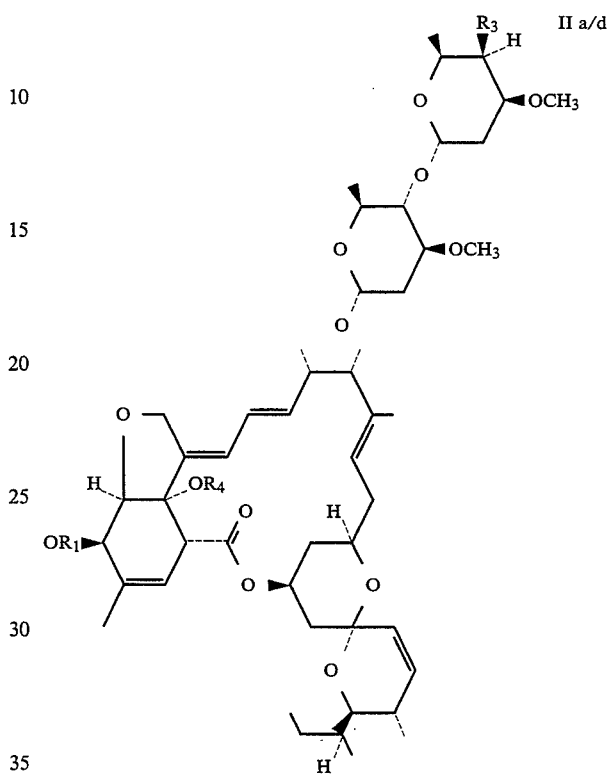

where $R^3$ is —$NHR^5$, wherein $R^5$ is —H or —$CH_3$; and $R^4$ is TMS; and (c) treating IIa/d ($R_1=CO_2CH_2CH=CH_2$) with $(Ph_3P)_4Pd(O)$ and $NaBH_4$ in a $C_{1-3}$ alkanol at a temperature of about 5° C. followed by treatment with a strong acid at about pH3; or if $R_1$=TBDMS, treating IIa/d with a strong acid at about pH3.

* * * * *